United States Patent [19]

Crane

[11] 4,044,253

[45] Aug. 23, 1977

[54] NON-DESTRUCTIVE INSPECTION OF COMPOSITE AND ADHESIVELY BONDED STRUCTURES

[75] Inventor: Robert L. Crane, Kettering, Ohio

[73] Assignee: The United States of America as represented by the Secretary of the Air Force, Washington, D.C.

[21] Appl. No.: 692,840

[22] Filed: June 4, 1976

[51] Int. Cl.² .............................................. G01N 21/16
[52] U.S. Cl. ................................. 250/302; 250/461 R
[58] Field of Search ............................... 250/302, 461

[56] References Cited

U.S. PATENT DOCUMENTS

| 3,506,827 | 4/1970 | Alburger | 250/302 |
| 3,857,033 | 12/1974 | Cobb | 250/302 X |
| 3,899,450 | 8/1975 | Molina | 250/302 X |

*Primary Examiner*—Archie R. Borchelt
*Attorney, Agent, or Firm*—Joseph E. Rusz; Cedric H. Kuhn

[57] ABSTRACT

Surface defects in composite and adhesively bonded structures that penetrate to a metal substrate are detected by applying a solution of 8-hydroxyquinoline to a surface of such a structure and viewing the surface under ultraviolet light. The presence of a flaw or crack leading from the surface to the metal substrate is indicated by a fluorescent glow.

7 Claims, No Drawings

NON-DESTRUCTIVE INSPECTION OF COMPOSITE AND ADHESIVELY BONDED STRUCTURES

RIGHTS OF THE GOVERNMENT

The invention described herein may be manufactured and used by or for the Government of the U.S. for all governmental purposes without the payment of any royalty.

FIELD OF THE INVENTION

This invention relates to a method for detecting flaws in nonmetallic coatings or skins bonded to metallic substrates.

BACKGROUND OF THE INVENTION

In industry several non-destructive techniques are used to determine if structural members are free of defects. For example, in the building industry, steel beams are inspected prior to use by ultrasonic and X-ray techniques to detect the possible presence of cracks. Structural members employed in the construction of aircraft are inspected for flaws both before and after their incorporation into an aircraft.

Several types of structural members are employed in the construction of aircraft. One type that is often used has a laminated structure which can be fabricated from one or more coatings or layers of a plastic material bonded with an adhesive or by a heat sealing procedure to a metal substrate. Another type of structural member has a honeycomb structure in which a layer in the form of a metallic honeycomb is sandwiched between two layers of plastic sheet material. The edges of the honeycomb layer are bonded to the sheets by means of an adhesive or by heat treatment.

As in the building industry, ultrasonic and X-ray test methods have been used to test structural members prior to their use in aircraft construction and periodically after operational use to determine if they are structurally sound. However, for several reasons such methods have not proven to be entirely satisfactory. For example, the methods involve the use of expensive and complicated equipment, requiring the services of skilled technicians. Simplified test procedures have been suggested for detecting minute surface defects that utilize dye penetrant compositions. Examples of such procedures are disclosed in U.S. Pat. Nos. 3,567,932, 3,814,695 and 3,896,664. While dye penetrants used in the prior art processes are effective in detecting surface defects, they are incapable of detecting whether a flaw penetrants to a metal substrate. In other words, the dye penetrants present the same appearance in the case of surface flaws as they do with through-the-thickness cracks. Since cracks penetrating to a metal substrate permit water and other corrosive elements to contact the substrate, it would be desirable to have an inspection method that distinguishes between mere surface defects and through-the-thickness cracks in a structural member.

It is a principal object of this invention, therefore, to provide a method for detecting flaws in composite structures comprising a metal substrate having a plastic skin or sheet bonded thereto that penetrate the skin or sheet to the substrate. Other objects and advantages of the invention will become apparent to those skilled in the art upon consideration of the accompanying disclosure.

SUMMARY OF THE INVENTION

This invention resides in a method for detecting through-the-thickness flaws in composites comprising a plastic sheet or coating bonded to a metal substrate. As used herein, the term "through-the-thickness flaw" indicates a crack or defect in a composite skin that extends from the skin's surface to the underlying metal substrate. The present method comprises the steps of applying a solution of 8-hydroxyquinoline in a solvent therefor to the plastic sheet or coating and then exposing the sheet or coating to ultraviolet radiation. The presence of through-the-thickness flaws in the plastic sheet or coating is indicated by a fluorescent glow.

In carrying out the method of this invention, minute surface defects that do not penetrate to the metal substrate do not fluoresce under ultraviolet light. However, if fluorescent penetrants are employed as in the processes described in the literature, fluorescence is observed for both surface defects and through-the-thickness flaws. Thus, the present method makes it possible to detect only those more serious defects which may admit corrosive elements to the composite's metal substrate. It is, of course, very important to detect through-the-thickness defects since the corrosion of an aircraft structural member could lead to structural failure. While it is not intended to restrict the present invention to any particular theory of operation, it is believed that the 8-hydroxyquinoline which is not itself a fluorescent penetrant, reacts with the metal substrate, thereby forming a metal chelate. The metal chelate so formed is a fluorescent penetrant which fluoresces when viewed under ultraviolet light. The method is particularly applicable to aircraft components, e.g., coated panels and honeycomb composites, in which the metal substrate is formed of aluminum, steel or brass.

As mentioned above, the 8-hydroxyquinoline is applied as a solution in a solvent therefor. While any suitable solvent can be employed, it is usually preferred to use water, an alcohol or mixtures thereof. Examples of alcohols that can be used include methanol, ethanol, isopropanol, and the like. The amount of 8-hydroxyquinoline contained in the solution can vary within rather broad limits although it is preferred to utilize at least about 0.001 weight percent, based upon the weight of the solvent. As a practical matter, the maximum amount employed does not exceed about 2.0 weight percent although larger amounts can be used. Thus, the amount of 8-hydroxyquinoline used generally ranges from about 0.001 to 2.0 weight percent, based upon the weight of the solvent.

The solution of 8-hydroxyquinoline can be applied to the surface of the structural member to be inspected by any of the well known, conventional procedures. It is often preferred to spray the solution on the surface, but it can be applied with a roller or brush. Also, the structural 8-hydroxyquinoline. can be dipped in a solution of the 8After applying the 8-hydroxyquinoline solution, a period of time sufficient for the solution to penetrate any cracks is allowed to elapse. Depending upon the thickness of the skin or coating bonded to the metal substrate, the soaking period usually ranges from about 10 seconds to 30 minutes. If desired, at the end of this period, excess solution can be removed from the surface merely by washing with water or an alcohol. Also, subsequent to the removal of excess solution, it is within the scope of the invention to air dry the surface for a period of time sufficient to dry the surface but insufficient to dry solution in any through-the-thickness cracks that may be present. The surface is then exposed to ultraviolet light and any through-the-thickness flaw is indicated by a fluorescent glow outlining the defect. Prior to exposure to the ultraviolet radiation, the surface can be coated with a dry developer. Developers are well known in the art and function to draw or blot residual traces of any metal chelate, which may be formed, out of any through-the-thickness defects in the structural member. As a result, any such defects are rendered more visible when viewed under ultraviolet light.

A more comprehensive understanding of the invention can be obtained by referring to the following illustrative example which is not intended, however, to be unduly limitative of the invention.

EXAMPLE

A portion of an F-4 aircraft rudder in the form of an aluminum honeycomb core having a boron-epoxy skin was inspected for defects in the skin that penetrated to the core. Initially, the rudder was placed horizontally on a table and the area to be inspected was wiped with paper towels soaked with a standard penetrant cleaner (Magnaflux ZC-7). The rudder was then examined under a Magnaflux ZB-26MF black light in a darkened room for any evidence of residual fluorescence. None was observed. A fine spray of a solution of 0.01 weight percent 8-hydroxyquinoline in isopropanol was applied to the surface of the rudder with an aspirator. After about 5 minutes, the rudder was again examined under ZB-26MF black light for evidence of fluorescence. A fluorescent halo was observed around a small hole in an area of the structure that contained a repair patch. The fluorescent halo indicated that the small hole penetrated to the aluminum honeycomb. (Subsequent destructive examination of the rudder confirmed this indication.) A standard penetrant developer (Magnaflux ZP-9) was then applied to the rudder by spraying near the fluorescent indication. The intensity of the fluorescent halo was thereby enhanced so that it could be readily photographed.

As seen from the foregoing example, the method of this invention makes it possible to detect through-the-thickness flaws in composite structures. Since processes using standard fluorescent penetrants do not distinguish between minor surface defects and through-the-thickness flaws, it is currently necessary to use radiography techniques when inspecting for such flaws. By utilizing the present method, inspection costs are materially decreased. Thus, it is unnecessary to employ expensive equipment requiring highly trained personnel since existing equipment and techniques employed with standard fluorescent penetrants can be utilized in practicing the method of this invention.

As will be evident to those skilled in the art, modifications of the present invention can be made in view of the foregoing disclosure without departing from the spirit and scope of the invention.

I claim:

1. A method for detecting through-the-thickness flaws in composites comprising a plastic sheet or coating bonded to a metal substrate which comprises the steps of applying to the sheet or coating a solution of 8-hydroxyquinoline in a solvent therefor; and exposing the sheet or coating to ultraviolet radiation.

2. The method according to claim 1 in which the solvent is selected from the group consisting of water, an alcohol, and mixtures thereof.

3. The method according to claim 2 in which the solvent is an alcohol selected from the group consisting of methanol, ethanol and isopropanol.

4. The method according to claim 1 in which the amount of 8-hydroxyquinoline ranges from about 0.001 to 2.0 weight percent, based upon the weight of the solvent.

5. The method according to claim 4 in which a period of time ranging from about 10 seconds to 30 minutes is allowed to elapse after applying the solution and prior to exposing the sheet or coating to ultraviolet radiation.

6. The method according to claim 5 in which the sheet or coating is covered with a coating of dry developer after applying the solution to the sheet or coating.

7. The method according to claim 6 in which the composite comprises an aluminum honeycomb core having a plastic sheet bonded thereto.

* * * * *

UNITED STATES PATENT AND TRADEMARK OFFICE
CERTIFICATE OF CORRECTION

PATENT NO. : 4,044,253

DATED : August 23, 1977

INVENTOR(S) : Robert L. Crane

It is certified that error appears in the above-identified patent and that said Letters Patent are hereby corrected as shown below:

Column 2, line 57 "8-hydroxyquinoline" should read -- member --; line 58, "8" should read -- 8-hydroxyquinoline. --. Column 3, line 36, after "honeycomb", insert -- core --. Column 4, in line 1 of claim 4, change "1" to -- 2 --.

Signed and Sealed this

Twenty-first Day of February 1978

[SEAL]

Attest:

RUTH C. MASON
*Attesting Officer*

LUTRELLE F. PARKER
*Acting Commissioner of Patents and Trademarks*